United States Patent
Stubbs et al.

(10) Patent No.: US 6,548,015 B1
(45) Date of Patent: Apr. 15, 2003

(54) SELF-SIMMERING FRAGRANCE DISPENSER

(76) Inventors: Jack B. Stubbs, 4266 Laura Marie Dr., Waynesville, OH (US) 45068; Andrea B. Stubbs, 4266 Laura Marie Dr., Waynesville, OH (US) 45068

( * ) Notice: Subject to any disclaimer, the term of this patent is extended or adjusted under 35 U.S.C. 154(b) by 0 days.

(21) Appl. No.: 09/456,761

(22) Filed: Dec. 7, 1999

(51) Int. Cl.$^7$ ................................................. A61L 9/00
(52) U.S. Cl. ........................... 422/5; 422/122; 422/123; 422/125
(58) Field of Search ............................ 422/5, 121, 123, 422/124, 125, 120, 122

(56) References Cited

U.S. PATENT DOCUMENTS

| | | | | |
|---|---|---|---|---|
| 4,088,751 A | * | 5/1978 | Kenkare et al. | 424/47 |
| 4,171,340 A | * | 10/1979 | Nishimura et al. | 422/36 |
| 4,264,362 A | | 4/1981 | Sergev et al. | 75/243 |
| 4,522,190 A | * | 6/1985 | Kuhn et al. | 126/263 |
| 4,781,895 A | * | 11/1988 | Spector | 422/125 |
| 4,849,181 A | * | 7/1989 | Kelley et al. | 422/109 |
| 5,041,421 A | * | 8/1991 | King | 512/4 |
| 5,593,635 A | * | 1/1997 | Matsumoto et al. | 422/5 |
| 5,593,792 A | | 1/1997 | Farrier et al. | 429/8 |
| 5,885,701 A | | 3/1999 | Berman et al. | |
| 5,916,528 A | * | 6/1999 | Matsumoto et al. | 422/125 |

* cited by examiner

*Primary Examiner*—Krisanne Thornton
(74) *Attorney, Agent, or Firm*—Dinsmore & Shohl LLP

(57) ABSTRACT

A method of dispensing fragrant vapor into the ambient. A container having a fragrant material and a reactant system therein is provided, wherein the reactant system generates heat when an aqueous solution is added to the container. An aqueous solution is then added to the container such that the reactant system generates heat which releases fragrant vapor. A device for dispensing fragrance is also provided.

28 Claims, 2 Drawing Sheets

SELF-SIMMERING FRAGRANCE DISPENSER

BACKGROUND OF THE INVENTION

I. Field of the Invention

The present invention is directed to a fragrance dispensing device which is activated by water. More particularly, one or more reactants in the device react with water and generate heat. The heat from this reaction activates aroma producing material within the device, thereby releasing the aroma into the ambient air.

II. Description of Related Art

Various devices have been developed over the years for releasing fragrance into the air. These devices are often used in homes, offices, or other enclosed areas in order to not only mask unpleasant odors, but also to add a pleasing fragrance into the air. Scented candles, for example, release fragrance from the melted wax. Burning candles, however, can be hazardous if left unattended, and are often prohibited in some areas (such as many office buildings).

"Potpourri" mixtures are also common. Traditional potpourri comprises various mixtures of aromatic herbs, dried flowers, and spices blended with essential oils, and release a fragrant scent into the air. Traditional potpourri is usually contained within a jar, a bowl, or a basket, and is placed in an area to mask unpleasant odors. An aroma is typically emitted in a very confined space, and lasts only a short time. Within a day, the potpourri mixture is dried up and ready to be discarded. Fragrant oils can be sprayed or dripped onto the potpourri to enhance the aroma, but again the area in which this is effective is very small.

Traditional potpourri may also be used with an external heat source and water to cause the scent to become airborne through the vaporization process of boiling the water. The potpourri mixture is typically placed in a pot of water, and the water is then heated. This technique is effective in making the aroma stronger and more widely spread. The disadvantage is that the heat source is either an electrical heating element or an open flame, both of which can be dangerous. The heated water becomes very hot. If it were to be spilled it could burn badly. In addition, if all of the water in the simmerer is vaporized, the potpourri material itself can be set on fire. The heat source itself is also dangerous, particularly if it is an open flame (such as a burning candle).

BRIEF DESCRIPTION OF THE DRAWINGS

While the specification concludes with claims particularly pointing out and distinctly claiming the present invention, it is believed that the same will be better understood from the following description taken in conjunction with the accompanying drawings in which:

SUMMARY OF THE PREFERRED EMBODIMENTS

Figure 1:
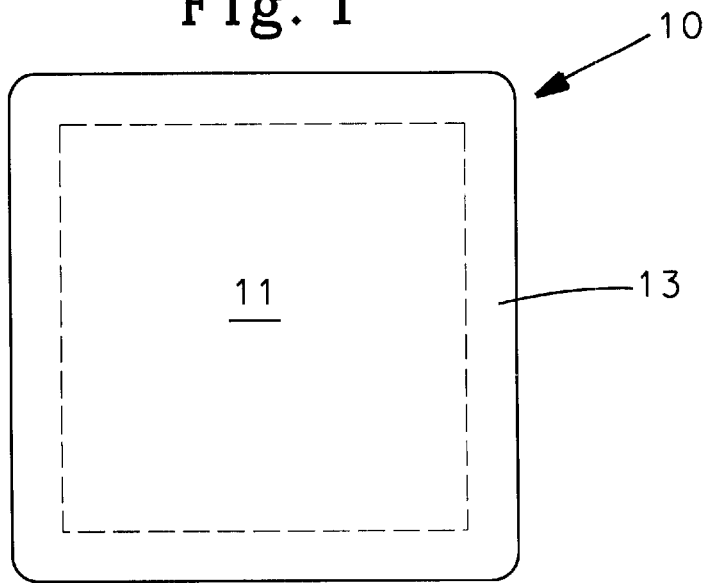
FIG. 1 is a top plan view of a fragrance dispensing device according to one embodiment of the present invention.

It is an object of the present invention to provide a fragrance dispensing device.

It is another object of the present invention to provide a fragrance dispensing device which requires no external heat source, and which may be activated by an aqueous solution.

It is yet another object of the present invention to provide a device which emits a fragrant vapor when an aqueous solution (such as water) is added to the device.

It is still another object of the present invention to provide a fragrance emitting device which employs an electrochemical heater in admixture with one or more fragrant materials which release fragrance upon heating (e.g., the heat volatilizes fragrant components of the fragrant material).

Additional objects, advantages and features of the present invention will be apparent to those skilled in the art upon examination of the specification herein. It should also be understood that the objects specifically identified above may or may not be provided by each and every embodiment of the present invention. Thus, these objects of the present invention are not to be construed as limiting in any way the scope of the claims appended hereto.

One embodiment of the present invention is a method of dispensing fragrant vapor into the ambient, comprising:

(a) providing a container having a fragrant material and a reactant system therein, wherein the reactant system generates heat when an aqueous solution is added to the container; and (b) adding an aqueous solution to the container such that the reactant system generates heat which releases fragrant vapor from the fragrant material.

The container may be porous, such that the step of adding an aqueous solution to the container comprises placing the porous container in an aqueous solution such that at least a portion of the aqueous solution; will absorbed into the container. By way of example, the container may be placed into a cup, bowl, tray or other receptacle containing an aqueous solution.

Alternatively, the step of adding an aqueous solution may comprise pouring an aqueous solution into the container, particularly when the container comprises a cup housing the reactant system and the fragrant material. When the container comprises a cup, a porous barrier member may be positioned above the fragrant material and the reactant system in order to prevent these materials from escaping from the container. The aqueous solution may simply be poured through the porous barrier member, and steam and fragrance will also escape through the porous barrier member.

The reactant system may comprise any of a variety of materials which release heat upon being activated by an aqueous solution, such as at least two metallic materials which electrochemically react in the presence of an electrolyte solution to generate heat. For example, the reactant system may comprise a supercorroding metallic mixture, such as a mixture of magnesium and iron (particularly a powdered mechanical alloy of magnesium and iron). An electrolyte (such as NaCl) may also be mixed with the metallic mixture, such that the reactant system may be activated by water alone. An absorbent material may also be provided in the container, wherein the fragrant material is absorbed onto (i.e., on the surface of or within) the absorbent material.

The present invention also provides a device for dispensing fragrance, comprising a container having therein:

(a) a reactant system which generates heat when an aqueous solution is added to the container; and (b) at least one fragrant material; wherein at least a portion of the container is porous. The container may have at least one wall comprising a porous material, wherein the porous material is chosen from the group consisting of: porous woven materials, porous non-woven materials, apertured sheets, and solid substrates having one or more apertures therein. For example, at least one wall of the container may comprise a porous, non-woven sheet, such as the type commonly used to manufacture tea bags. In fact, the container may comprise a pouch made from a tea bag material. The reactant system may be as described above, and may include an electrolyte in the container. In addition, the container may further include therein an absorbent material, wherein the fragrant material is absorbed onto the absorbent material. Suitable absorbent materials include: vermiculite, ground corn cobs, clay, wood pulp, saw dust, and particulate cellulose (i.e., particulate plant matter).

The fragrant material may include one or more fragrant liquids and/or one or more fragrant plant materials. Suitable fragrant liquids includes various fragrant oils (including essential oils), as well as other plant extracts (including extracts from flowers and fruits), and synthetic fragrant liquids. Suitable fragrant plant materials include dried flowers, dried fruit, spices (e.g., ground cinnamon), and herbs (e.g., rosemary). These plant materials may be ground or pulverized to facilitate their inclusion in the container. Of course it will be understood that a variety of fragrant materials may be employed depending upon the desired fragrance. Even insect-repelling fragrant materials may be used (such as citronella oil), thus providing a device and method for repelling insects.

Another embodiment of the present invention comprises a device for dispensing fragrance, comprising a container housing a fragrant material and a reactant system which generates heat when an aqueous solution is added to the container, wherein the container is configured such that an aqueous solution may be added to the container in order to generate heat within the container and dispense fragrance from the container into the ambient. The container may further include a porous barrier member configured such that an aqueous solution may be added to the container through the porous barrier member.

DETAILED DESCRIPTION OF THE INVENTION

Figure 2:
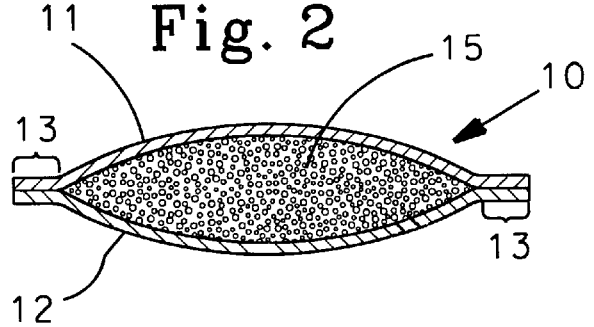
FIG. 2 is a cross-sectional view of the device of FIG. 1, taken along line 2—2 thereof.

Referring now to the drawings in detail, wherein like numerals indicate similar elements throughout the views, FIGS. 1 and 2 depict a fragrance dispensing device according to one embodiment of the present invention. The fragrance dispensing device of FIGS. 1 and 2 generally comprises a porous container 10 which houses a fragrant material (i.e., an aroma producing material) and a reactant system which will react and produce heat. When container 10 is placed in a volume of water, water is absorbed into the container activates the reactant system, resulting in the generation of heat. The heat produced within container 10 will cause fragrance to be released from the fragrant material into the ambient, thereby providing a fragrance (or scent) in the area in which the device is located. In particular, the fragrance dispensing device is configured to dispense fragrant vapor into one or more rooms (such as a room of a house or even an office), or other enclosed area (such as a vehicle; e.g., an automobile).

Heat generated within container 10 causes vapor to be released from the fragrant material (e.g., by volatilizing one or more components of the fragrant material). In addition, water absorbed into container 10 may even boil as a result of the heat generated in container 10, thereby releasing steam to the atmosphere. The generated steam may also assist in dispensing fragrant vapor from container 10, and may even improve the dispersion of the fragrance into the surrounding atmosphere. In this manner, the present invention provides a self-simmering potpourri device that requires no external heat source in order to release fragrant vapor into the air. There is no open flame or other exposed heat source, as only water is required to activate the device, and any boiling water remains within container 10. In addition, the reactant system may be chosen such that the reaction products are safe, and non-toxic.

As used herein, the term "fragrance" is not limited to pleasant smells, but is intended to include scents which function, for example, as insecticides or deodorants (including scents which may be undetectable by the human olfactory system, such as scents used to attract or repel certain animals). However, one particular embodiment of the present invention comprises an air freshener for masking unpleasant odors (such as tobacco smoke) by emitting a pleasing fragrance. Another embodiment of the present invention comprises an aromatherapy device which emits aromatherapy fragrances (such as those emitted by various essential oils used for aromatherapy). Yet another embodiment comprises an insect repelling device which emits an insect repelling fragrance.

The porous container of the fragrance dispensing device according to one embodiment of the present invention may comprise any of a variety of structures having a porous region which allows water to be absorbed into the container. For example, container 10 may comprise a multi-walled structure, wherein at least one of the walls (or a portion of at least one of the walls) is porous. Thus, the term "porous container" simply means that at least a portion (or region) of the container is porous (i.e., liquid permeable) such that water may be absorbed into the container, and steam and fragrant vapor can escape from the container. Suitable porous materials include woven and non-woven materials (such as porous, woven and non-woven webs or sheets of material), apertured or perforated sheets or films, as well as solid substrates (such as metal, glass, ceramic, or other polymeric material) having one or more apertures therein. Preferably, the porous material should be configured such that the solid materials in the container (e.g., reactants and fragrant materials) will not escape from the container).

In the embodiment shown in FIGS. 1 and 2, the entire container 10 is porous, and is made from a non-woven material of the type used in the manufacture of tea bags (such as Dexter #11681 non-woven paper, available from the T. H. Dexter Co. of Windsor Locks, Conn.). Thus, as best seen in FIG. 2, container 10 is formed from upper sheet 11 and lower sheet 12, which are sealed to one another about their periphery 13 in order to provide an interior volume 15 therebetween. Sheets 11 and 12 may be sealed to one another, for example, by means of an adhesive, particularly a heat-activated adhesive of the type used in the manufacture of tea bags. In fact, the fragrance dispensing device shown in FIGS. 1 and 2 can even be produced using conventional tea-bag filling machines. It should also be pointed out that container 10 may be made from a single sheet of material (e.g., a non-woven material) which is folded in half and then sealed about its periphery to form container 10. In other words, one edge of the container will be provided by a fold, rather than the sealing of one sheet to another. It should also be pointed out that various printed indicia (such as a fragrance description) may be printed on container 10. Company logos may even be printed on container 10 for promotional purposes.

Figure 4:
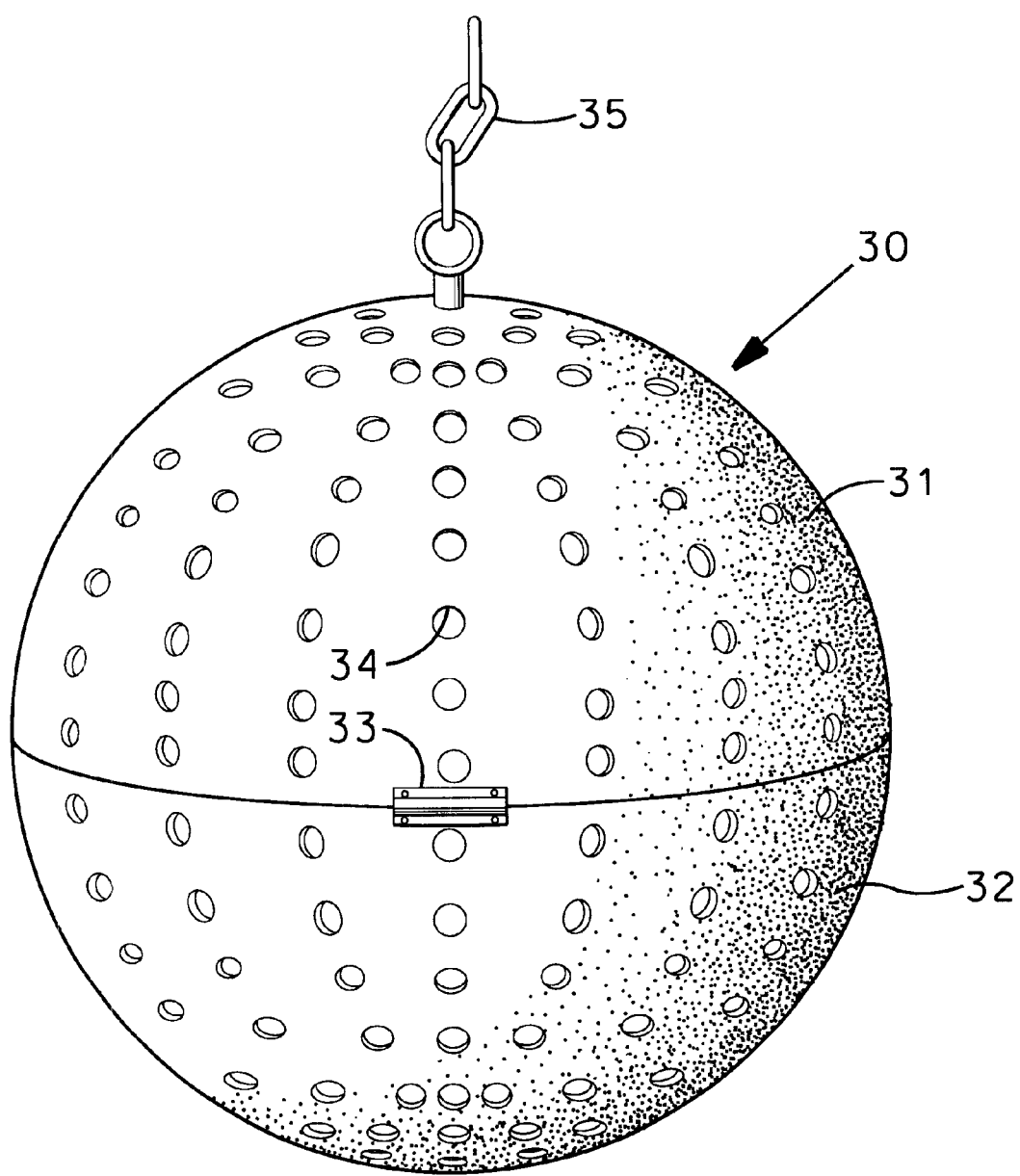
FIG. 4 is a perspective view of a fragrance dispensing device according to yet another alternative embodiment of the present invention.

As an alternative to the pouch or tea-bag like structure shown in FIGS. 1 and 2, the porous container may comprise a variety of other configurations. Thus, the porous container (or a portion thereof) may be formed from a solid substrate having a plurality of apertures formed therein. Thus, as shown in FIG. 4, the porous container may comprise a hollow, foraminous container 30 into which the reactants and fragrant material may be placed. Container 30 is similar to a conventional "tea ball," and may be formed from a top half 31 and a bottom half 32 which are joined together at hinge 33. A clasp may also be provided on the side opposite hinge 33 such that container 30 may be opened for filling and closed for use. Thus, container 30 is configured for refilling and reuse, similar to the manner in which a tea-ball may be reused. Container 30 may be made, for example, from stainless steel or other suitable material. A plurality of apertures 34 are provided on container 30, and allow water to enter the interior volume of container 30, and allow steam and fragrant vapor to escape into the ambient. Apertures 34 should be small enough, however, to prevent the reactants and fragrant materials from escaping.

Alternative materials for foraminous containers suitable for use in the present invention include metals (such as stainless steel), ceramics (such as porcelain), glass, high temperature papers, rubbers and plastics. Thus, the porous container may comprise any structure having a porous region or portion (such as a wall of the container) which allows water, steam and fragrant vapor to pass therethrough, and an interior volume configured for housing the reactant system and fragrant material therein.

A variety of reactant systems may be used in the fragrance dispensing device of the present invention. The reactant system should generally include one or more reactants which react in water such that heat is generated. Suitable reactant systems include those comprising two or more metallic materials (e.g., pure metals, metal alloys, and/or metallic compounds which interact electrochemically to generate heat (such as supercorroding metallic materials). One metallic material acts as an anode, while the another acts as a cathode. An electrolyte solution is used to initiate the reaction, particularly an aqueous electrolyte solution. The electrolyte may be provided in the container itself, along with the other reactants, or may be provided by an aqueous electrolyte solution (e.g., salt water). The metallic materials of the reactant system may be provided in a variety of forms, such as a mixture of powders (including powdered, mechanical alloys of the metallic materials), frozen melts or even solid structures formed from the metallic materials.

By way of example, powdered mechanical alloys of two or more distinct metals may be employed (also known as supercorroding metallic alloys). In particular, magnesium or aluminum may serve as the anode material, whereas iron or nickel may serve as the cathode material. Other suitable metallic cathode materials include copper, cobalt, palladium, silver, gold or platinum. Preferably, a powdered mechanical alloy of magnesium and iron is employed, wherein various ratios of the two materials may be employed. The ratio of magnesium to iron (or alternatively nickel) may be chosen to provide the desired amount of heating. Preferably, magnesium is present in a greater amount. More preferably, magnesium comprises between about 80 and about 95 atomic percent of the powdered mechanical alloy (with the remainder comprising iron or nickel). Such materials are well-known in the art, and their production is described, for example, in U.S. Pat. No. 4,264,362 (which is incorporated herein by reference). Suitable powdered alloys of magnesium and iron are available, for example, from Zestotherm, Inc. of Cincinnati, Ohio.

The above-described supercorroding metallic materials are generally activated by an electrolyte solution, such as a salt (e.g., KCl, NaCl and/or $CaCl_2$) dissolved in water. While the devices of the present invention may be activated by adding an electrolyte solution to the container (such as a brine solution), it is preferred that a salt (preferably NaCl) be included in the container along with the supercorroding metallic materials. Thus, a small amount of dry NaCl (or other salt) may be mixed with a powdered mechanical alloy of magnesium and iron, and the mixture then placed into container 10. In this manner, water alone will activate the reactant system (i.e., by providing an electrolyte solution within the container). Only a small amount of salt is needed. For example, container 10 may include a sufficient amount of salt to provide an electrolyte solution having a salt concentration of at least about 0.5 weight percent (based upon the quantity of water absorbed into container 10).

The type and amount of the reactant system within container 10 may be selected in order to control the amount of heat generated. Preferably, a sufficient amount of the reactant system is included to cause controlled boiling of the water absorbed into container 10, such that the water will continue boiling for an extended period of time (e.g., more than a few minutes). In a preferred embodiment, at least about 0.5 ounces of the reactant system (powdered alloy and NaCl) is included in container 10, more preferably between about 0.5 and about 5 ounces. The amount of fragrant material may be varied as desired, and will depend upon the type and concentration of fragrant materials employed.

The type and number of fragrant materials which may be employed in the fragrance dispensing devices of the present invention is numerous. In general, the fragrant materials employed should be such that fragrant vapor is released from the fragrant material upon heating (the heat volatilizes one or more components of the fragrant material). It should be pointed out, however, that most suitable fragrant materials will emit some fragrance even without heating. However, upon heating, the amount of fragrance emitted from the fragrant material will increase (e.g., due to an increase in vapor pressure of the fragrant material). Liquid and/or solid fragrant materials may be employed.

Natural and synthetic liquid fragrant materials may be used, including, for example, natural fragrant oils (such as essential oils), plant or fruit extracts or distillates, discrete chemical compounds (such as various esters, lactones or ketones), and aqueous fragrant solutions. A variety of fragrant oils and other fragrant liquids are commercially available (both natural and synthetic), particularly those used in conventional potpourri products. These oils are typically formulated to provide a variety of pleasing aromas, such as: amber, apple, bayberry, bay rum, bitter almond, blueberry, blue magnolia, bubble gum, candy cane, cappuccino, carnation, coconut, chocolate, mocha, citrus punch, lilac, cucumber, eucalyptus, frankincense, gingerbread, heather, honeysuckle, jasmine, musk and pumpkin pie. Suitable oils are available, for example, from ReneaL, The Flower Petal and Fragrance Supply Shop, of Erie, Colo.

Suitable solid fragrant materials include fragrant plant or fruit materials, such as dried flowers, dried fruit, spices (e.g., ground cinnamon), and herbs (e.g., rosemary). Exemplary solid fragrant materials include the following materials, which may be ground or pulverized prior to their inclusion in the devices according to the present invention: coco flowers, cinnamon, vanilla bean, hibiscus flowers, hollyhock flowers, karni, fern, rose leaves, tilia flowers, cloves, pine needles, cranberries, rhododendron leaves, rose hips, allspice, anise, casurina, and pomegranate.

The fragrance(s) emitted by the device of the present invention can be used to mask unpleasant odors, or otherwise condition the atmosphere surrounding the device. In addition, the fragrant material can comprise one or more aromatherapy materials. While some aromas released into the air are pleasing and give enjoyment to those who smell them, others are believed to have medicinal properties. Suitable aromatherapy fragrant materials include essential oils extracted from the following plants: ammi visnaga, angelica archangelica, basil linalol, ocimum basilicum, pimenta racemosa, laurus nobilis, bergamot, mint, mentha citrada, melaleuca cajeputi, daucus carota, cedrus atlantica, virginiana, chamomile, cistus ladanifer, salvia sclarea, citrus clementina, petitgrain, clove bud, coriandrum sativum, cypress, eucalyptus, fennel, frankincense, galanum, helichrysum italicum, lemon teatree, and vanilla.

Container 10 may also include an absorbent material therein, particularly when one or more liquid fragrant materials are employed. The liquid fragrant material may be absorbed into the absorbent material, such that the liquid fragrant material may be retained within container 10. Any of a variety of absorbent materials may be used. By way of example, particulate absorbent materials such as vermiculite, ground corn cobs, clay, wood pulp, saw dust, or other cellulose materials may be employed. The absorbent material may be soaked in one or more liquid fragrant materials, and/or one or more liquid fragrant materials may be sprayed onto the absorbent materials. Thereafter, the impregnated absorbent material is then placed into container 10, and may be mixed with the reactant system prior thereto. Alternatively, liquid fragrant material may even be absorbed into the walls of the container itself, or sprayed onto one or more of the reactant materials.

Once container 10 has been filled with the reactant system and one or more fragrant materials and sealed, the container may simply be placed into a volume of an aqueous solution (such as a cup, bowl, tray or other receptacle containing an aqueous solution). If an electrolyte (such as NaCl) is not provided in the container, the aqueous solution should include an electrolyte (such as NaCl) dissolved therein. Water is absorbed into container 10, wherein the water will activate the reactant system. The absorbed water will soon begin to boil (typically after about 60 seconds), thus emitting steam and fragrant vapor from container 10. When the tea-bag like structure of FIGS. 1 and 2 is employed, container 10 will float on the surface of the volume of water, facilitating the release of fragrant vapor into the atmosphere. The receptacle into which container 10 is placed is preferably configured to allow container 10 to freely float on the surface of the aqueous solution. In addition, the volume of the aqueous solution may even be sized such that the entire volume is absorbed by container 10 (thus reducing the amount of heat lost to the unabsorbed portion of the aqueous solution). Although the volume of steam released from container 10 will generally subside after 5–30 minutes (depending in part upon the volume and type of reactant system employed), fragrant vapor will continue to the dispensed from container 10 for a longer period of time (e.g., 3–4 hours) due to the continued generation of heat within container 10 (and the elevated temperature within container 10). Once the release of fragrant vapor from container 10 has ceased, container 10 may be discarded.

In general, only the water absorbed into container 10 will boil, and that portion of the volume of water not absorbed into container 10 will not heat significantly. Thus, when container 10 is dropped into a cup or other volume of water, the cup may be picked up by hand with little or no danger of burns. Even if the cup spills, the spilt water will not cause burns or result in a fire hazard. Container 10, however, will become warm, and handling container 10 should be avoided (at least during the initial period of reaction). In addition, the byproducts of the electrochemical reaction are generally safe and non-toxic. For example, when the reactant system comprises a powdered alloy of magnesium and iron, the reaction product will comprise magnesium hydroxide (a common antacid).

Figure 3:
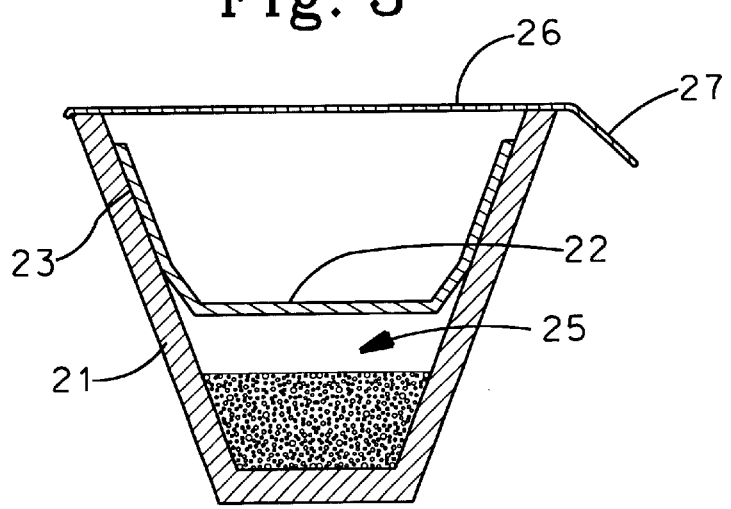
FIG. 3 is a cross-sectional view of a fragrance dispensing device according to an alternative embodiment of the present invention.

An alternative embodiment of a fragrance dispensing device according to the present invention is depicted in FIG. 3, and comprises a container 21 having an internal volume 25. A mixture of one or more fragrant materials, and a reactant system is provided in container 21, as shown. In the embodiment of FIG. 2, container 21 essentially comprises a cup, and may be made from any of a variety of materials (such as styrofoam, or other insulating material). In order to activate the device, water may be added to container 21 by simply pouring water into the container. If an electrolyte (such as NaCl) is not provided in container 21, brine (i.e., salt water) may be poured into container 21 to activate the device. Upon activation, steam and fragrant vapor will be dispensed from container 21 into the atmosphere.

A porous barrier member 22 may also be provided in order to enclose internal volume 25 of container 21. In this manner, the reactant system and the fragrant materials will be retained within container 25. Porous barrier member 22 may be made from a variety of materials, including woven and non-woven materials (such as a porous non-woven material of the type used to manufacture tea bags or filter paper). Barrier member 22 may be sealed to container 21 around periphery 23 of barrier member 22 (such as by an adhesive). Due to the porous nature of barrier member 22, water poured into container 21 will pass through barrier member 22 into internal volume 25 housing the reactant system and the fragrant material.

A removable sealing member 26 may also be provided on container 21 in order to prevent moisture from entering into container 21. Sealing member 26 preferably comprises a non-porous material, such as a metallic foil, and may be adhered to the top surface of container 21 by means of an adhesive. Prior to use, sealing member 26 may be removed from container 21 or penetrated in order to allow water to be poured into container 21 (such as by cutting an opening therein, or otherwise puncturing sealing member 26). A pull tab 27 may be provided on sealing member 26 in order to facilitate the removal of sealing member 26 from container 21.

It will be understood that the specific embodiments of the present invention shown and described herein are merely exemplary, as the present invention may be provided in a variety of alternative embodiments. Accordingly, the scope of the present invention should be considered in terms of the following claims, and it is understood not to be limited to the details of the structure and operation shown and described in the specification and the drawings.

What we claim is:

1. A method of dispensing fragrant vapor into the ambient, comprising:
   (a) providing a container having a fragrant material absorbed onto an absorbent material and a reactant system therein, wherein said reactant system generates heat when an aqueous solution is added to the container; and
   (b) adding an aqueous solution to said container such that said reactant system generates heat which releases fragrant vapor from said fragrant material.

2. The method of claim 1, wherein said container comprises a porous container, and said step of adding an aqueous solution to said container comprises placing said porous container in an aqueous solution such that at least a portion of the aqueous solution is absorbed into said container.

3. The method of claim 1, wherein said step of adding an aqueous solution comprises pouring an aqueous solution into said container.

4. The method of claim 3, wherein said container comprises a cup, and wherein said container further includes a porous barrier member positioned above said fragrant material and said reactant system.

5. The method of claim 1, wherein said reactant system comprises at least two metallic materials which electrochemically react in the presence of an electrolyte solution to generate heat.

6. The method of claim 5, wherein said reactant system comprises magnesium and iron.

7. The method of claim 6, wherein said reactant system further comprises an electrolyte, and said aqueous solution comprises water.

8. The method of claim 7, wherein said reactant system comprises a powdered mechanical alloy of magnesium and iron, said electrolyte comprises NaCl.

9. A device for dispensing fragrance, comprising a container having therein:
   (a) a reactant system which generates heat when an aqueous solution is added to the container; and
   (b) at least one fragrant material, wherein the fragrant material is mixed together with the reactant system in the container; wherein at least a portion of said container is porous.

10. The device of claim 9, wherein said container has at least one wall comprising a porous material, and wherein said porous material is chosen from the group consisting of: porous woven materials, porous non-woven materials, apertured sheets, and solid substrates having one or more apertures therein.

11. The device of claim 10, wherein at least one wall of said container comprises a porous, non-woven sheet.

12. The device of claim 11, wherein said container comprises a pouch made from a porous, non-woven material.

13. The device of claim 9, wherein said reaction system comprises a supercorroding metallic mixture.

14. The device of claim 13, wherein said reaction system comprises a powdered alloy of magnesium and iron.

15. The device of claim 14, wherein said container further includes an electrolyte therein.

16. The device of claim 9, wherein said container further includes therein an absorbent material, and wherein said fragrant material is absorbed onto said absorbent material.

17. The device of claim 16, wherein said absorbent material is chosen from the group consisting of: vermiculite, ground corn cobs, clay, wood pulp, saw dust, and particulate cellulose.

18. The device of claim 9, wherein said fragrant material is chosen from the group consisting of: fragrant liquids and fragrant plant material.

19. The device of claim 11, wherein said fragrant material comprises an essential oil.

20. A device for dispensing fragrance, comprising a container housing a fragrant material and a reactant system which generates heat when an aqueous solution is added to the container, wherein the fragrant material and reactant system are mixed together in said container, and wherein said container includes a porous barrier member and is configured to accept an aqueous solution through said porous barrier member in order to generate heat within said container and dispense fragrance from said container into the ambient through said porous barrier member.

21. The device of claim 20, wherein said reaction system comprises a supercorroding metallic mixture.

22. The device of claim 21, wherein said reaction system comprises a powdered alloy of magnesium and iron.

23. The device of claim 20, wherein said container further includes an electrolyte therein.

24. The device of claim 20, wherein said container further includes therein an absorbent material, and wherein said fragrant material is absorbed into said absorbent material.

25. The device of claim 20, wherein said fragrant material is chosen from the group consisting of: fragrant liquids and fragrant plant material.

26. The device of claim 25, wherein said fragrant material comprises an essential oil.

27. The device of claim 20, wherein said fragrant material comprises a material which, when heated, releases an insect-repelling fragrance.

28. The device of claim 20, wherein said container comprises a pouch made from a porous, non-woven material.

* * * * *